United States Patent
Kato et al.

(10) Patent No.: US 10,745,296 B2
(45) Date of Patent: Aug. 18, 2020

(54) FLUID PROCESSING APPARATUS HAVING MULTIPLE RECTIFYING PLATES

(71) Applicant: STANLEY ELECTRIC CO., LTD., Tokyo (JP)

(72) Inventors: Hiroyuki Kato, Tokyo (JP); Junji Matsuda, Tokyo (JP); Naoko Matsumoto, Tokyo (JP); Tomoaki Kodama, Tokyo (JP)

(73) Assignee: STANLEY ELECTRIC CO., LTD., Tokyo (JP)

( * ) Notice: Subject to any disclaimer, the term of this patent is extended or adjusted under 35 U.S.C. 154(b) by 0 days.

(21) Appl. No.: 16/279,835

(22) Filed: Feb. 19, 2019

(65) Prior Publication Data

US 2019/0256379 A1    Aug. 22, 2019

(30) Foreign Application Priority Data

Feb. 20, 2018    (JP) .................. 2018-027757

(51) Int. Cl.
*C02F 1/32* (2006.01)
*B01F 5/06* (2006.01)
(Continued)

(52) U.S. Cl.
CPC .............. *C02F 1/325* (2013.01); *A61L 2/10* (2013.01); *B01F 5/0604* (2013.01); *B01F 5/0688* (2013.01); *B01J 19/006* (2013.01); *B01J 19/123* (2013.01); *B01J 19/2415* (2013.01); *B01F 2215/0036* (2013.01); *B01J 2219/00768* (2013.01); *B01J 2219/1925* (2013.01); *B01J 2219/1947* (2013.01);
(Continued)

(58) Field of Classification Search
CPC .............. C02F 1/325; C02F 2201/3222; C02F 2201/328; C02F 2303/04; A61L 2/10; B01F 5/0604; B01F 5/0688; B01F 2215/0036; B01J 19/006; B01J 19/123; B01J 19/2415; B01J 2219/00768; B01J 2219/1925; B01J 2219/1947
See application file for complete search history.

(56) References Cited

U.S. PATENT DOCUMENTS

2006/0231503 A1    10/2006    Flettner
2011/0024365 A1*   2/2011    Yong .................. C02F 1/325
                                                            210/748.1
2015/0114912 A1    4/2015    Taghipour

FOREIGN PATENT DOCUMENTS

CN    201932930 U    8/2011
JP    2007-152155 A    6/2007
(Continued)

OTHER PUBLICATIONS

The extended European Search Report for the related European Patent Application No. 19158104.0 dated Jul. 18, 2019.

*Primary Examiner* — Nicole M Ippolito
*Assistant Examiner* — Hanway Chang
(74) *Attorney, Agent, or Firm* — Kenealy Vaidya LLP

(57) ABSTRACT

A fluid processing apparatus includes: a casing having a fluid inlet pipe and a fluid outlet pipe; multiple rectifying plates with holes in parallel with each other provided within the casing on a side of the fluid inlet pipe, the rectifying plates being perpendicular to a longitudinal axis of the casing; and a light source for irradiating fluid passing from the fluid inlet pipe through the casing to the fluid outlet pipe with ultraviolet rays.

19 Claims, 15 Drawing Sheets

(51) Int. Cl.
 *B01J 19/24* (2006.01)
 *A61L 2/10* (2006.01)
 *B01J 19/12* (2006.01)
 *B01J 19/00* (2006.01)

(52) U.S. Cl.
 CPC .................. *C02F 2201/328* (2013.01); *C02F 2201/3222* (2013.01); *C02F 2303/04* (2013.01)

(56) References Cited

FOREIGN PATENT DOCUMENTS

| | | |
|---|---|---|
| JP | 2017-051290 A | 3/2017 |
| JP | 2017-087104 A | 5/2017 |
| WO | 2005/105675 A1 | 11/2005 |

* cited by examiner

Fig.6
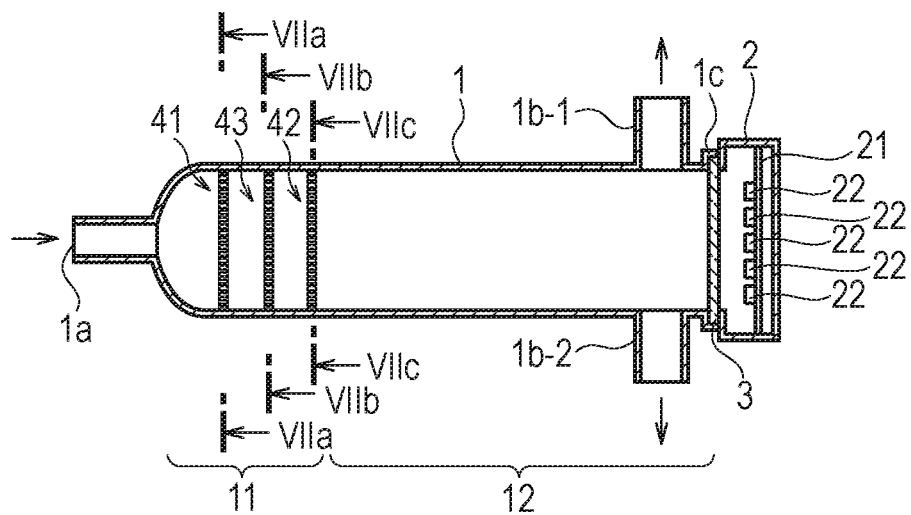
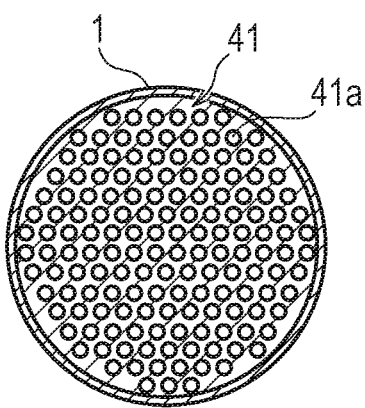
Fig.7A
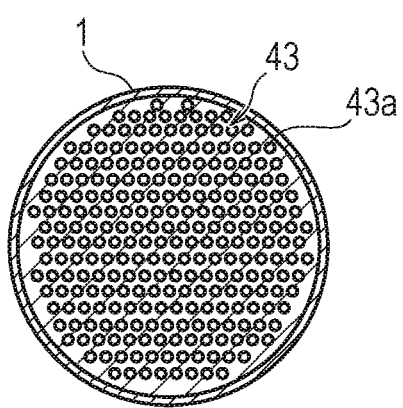
Fig.7B
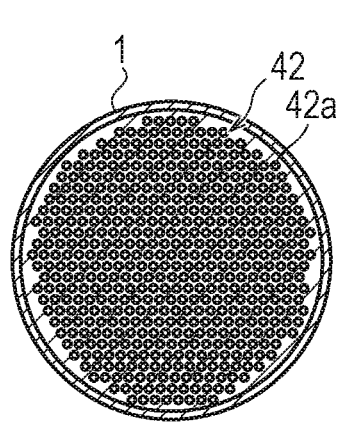
Fig.7C

FLUID PROCESSING APPARATUS HAVING MULTIPLE RECTIFYING PLATES

This application claims the priority benefit under 35 U.S.C. § 119 to Japanese Patent Application No. JP2018-027757 filed on Feb. 20, 2018, which disclosure is hereby incorporated in its entirety by reference.

BACKGROUND

Field

The presently disclosed subject matter relates to a fluid processing apparatus using ultraviolet rays.

Description of the Related Art

Generally, a fluid processing apparatus using ultraviolet rays with a short wavelength of about 240 to 380 nm is used as a fluid sterilizer, a fluid disinfector, a fluid purifier and so on.

A first prior art fluid processing apparatus is constructed by a casing serving as a fluid passage along its longitudinal axis direction, a light source for irradiating fluid within the fluid passage with ultraviolet rays, and a hollow fiber membrane filter provided within the casing on the upstream side thereof for changing the fluid stream from a turbulence flow state to a laminar flow state (see: JP2017-87104A). Therefore, fluid in the laminar flow state can be irradiated uniformly with ultraviolet rays, thus enhancing the processing efficiency of fluid.

In the above-described first prior art fluid processing apparatus, however, when the hollow fiber membrane filter is clogged due to aging, the laminar flow rate of fluid is non-uniform, so that the processing efficiency of the fluid processing apparatus would deteriorate.

A second prior art fluid processing apparatus is constructed by a single rectifying plate with small holes instead of the hollow fiber membrane filter of the first prior art fluid processing apparatus (see: JP2017-51290A). Therefore, the fluid stream is also changed by the single rectifying plate from a turbulence flow state to a laminar flow state, thus enhancing the processing efficiency of the fluid processing apparatus.

In the above-described second prior art fluid processing apparatus, although the flow rate of fluid in the proximity of the inner face of the casing is relatively small, the flow rate of fluid in the center of the casing is relatively large, so that the fluid flowing through the center of the casing would not be sufficiently irradiated with ultraviolet rays.

SUMMARY

The presently disclosed subject matter seeks to solve one or more of the above-described problems.

According to the presently disclosed subject matter, a fluid processing apparatus includes: a casing having a fluid inlet pipe and a fluid outlet pipe; multiple rectifying plates with holes in parallel with each other provided within the casing on a side of the fluid inlet pipe, the rectifying plates being perpendicular to a longitudinal axis of the casing; and a light source for irradiating fluid passing from the fluid inlet pipe through the casing to the fluid outlet pipe with ultraviolet rays.

According to the presently disclosed subject matter, since there are multiple rectifying plates, fluid passed through the multiple rectifying plates can become in a laminar flow state whose average flow rate is low, so that the fluid would be equally irradiated with ultraviolet rays.

BRIEF DESCRIPTION OF THE DRAWINGS

The above and other advantages and features of the presently disclosed subject matter will be more apparent from the following description of certain embodiments, taken in conjunction with the accompanying drawings, wherein:

FIG. 6 is a cross-sectional view illustrating a modification of the fluid processing apparatus of FIG. 2;

FIGS. 7A, 7b and 7C are transverse cross-sectional views taken along the lines VIIa-VIIa, VIIb-VIIb and IIIc-IIIc, respectively, in FIG. 6;

DETAILED DESCRIPTION OF EXEMPLARY EMBODIMENTS

Figure 1:
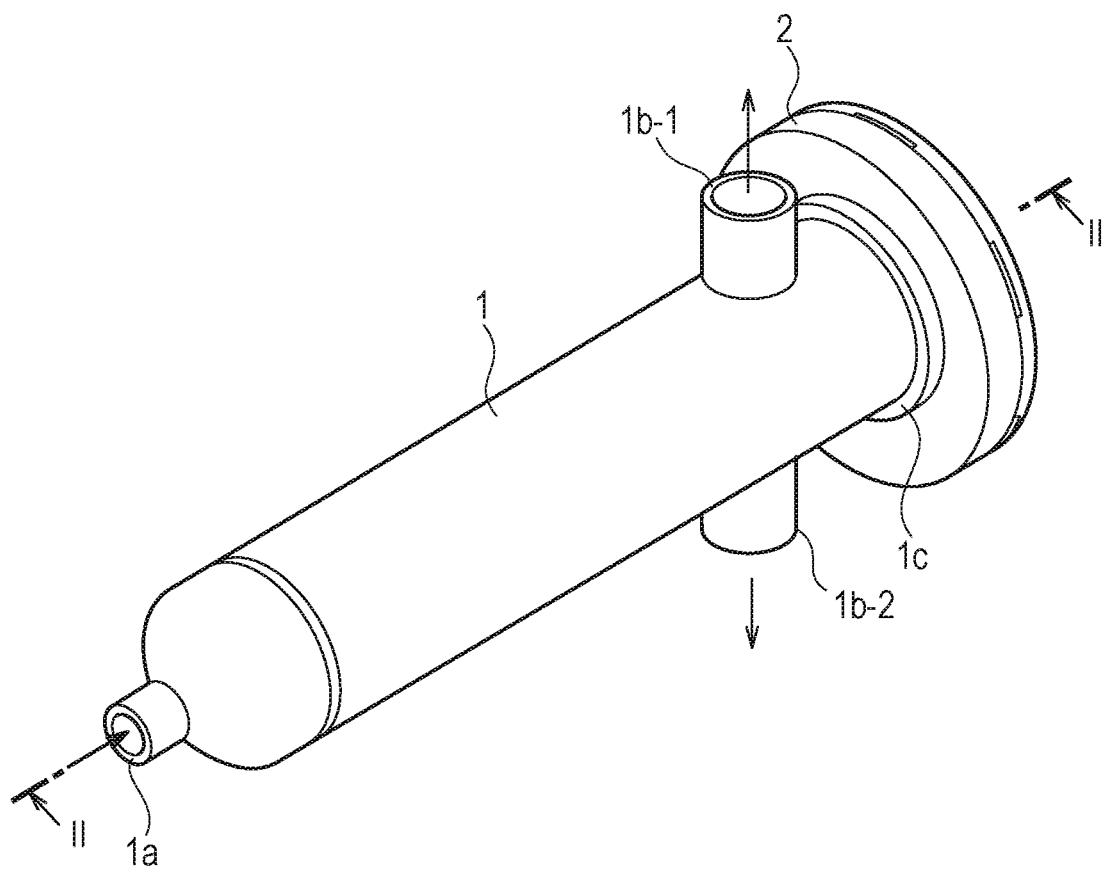
FIG. 1 is a perspective view illustrating a first embodiment of the fluid processing apparatus according to the presently disclosed subject matter.
Figure 2:
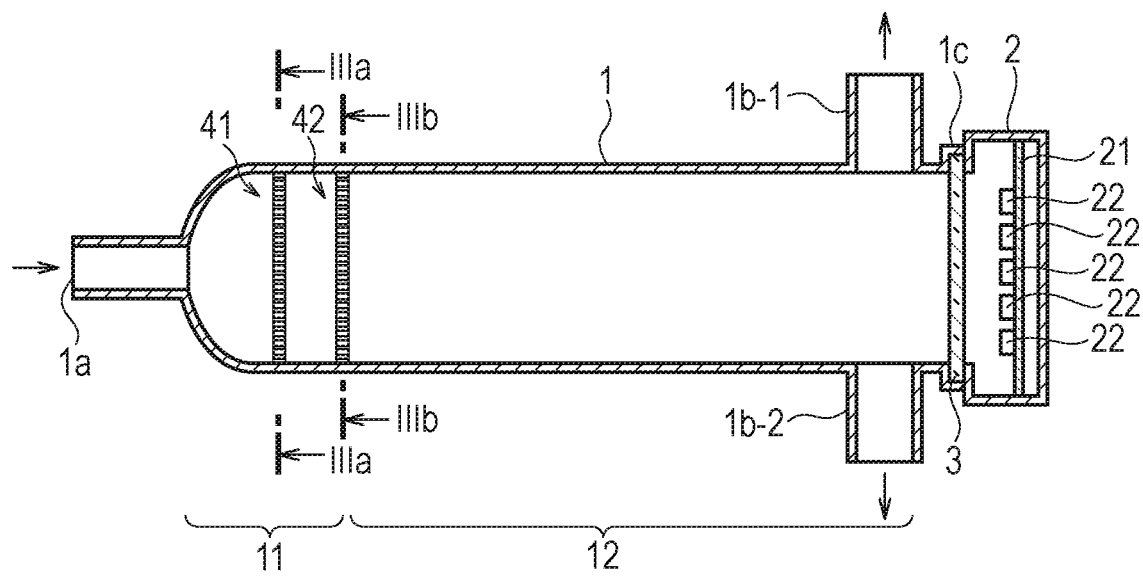
FIG. 2 is a longitudinal cross-sectional view taken along the line II-II in FIG. 1.

FIG. 1 is a perspective view illustrating a first embodiment of the fluid processing apparatus according to the presently disclosed subject matter, and FIG. 2 is a longitudinal cross-sectional view taken along the line II-II in FIG. 1.

In FIGS. 1 and 2, the fluid processing apparatus is constructed by a cylindrical casing 1 for passing fluid to be processed therethrough and a light-emitting diode (LED) accommodating chamber 2 adhered to an aperture 1c of the casing 1 on the downstream side. The casing 1 and the LED accommodating chamber 2 are partitioned by an ultraviolet transmitting window 3 which is mounted on the aperture 1c of the casing 1.

The casing 1 is a cylindrical straight pipe made of stainless, Teflon (trademark) resin or the like having an inner diameter of 134 mm, for example, and an outer diameter of 140 mm, for example, and is about 580 mm long. The casing 1 is provided with a fluid inlet pipe 1a on the upstream side whose diameter is 43 mm, for example, and fluid outlet pipes 1b-1 and 1b-2 on the downstream side whose diameter is 43 mm, for example. The flow rate of fluid passing from the fluid inlet pipe 1a through the casing 1 to the fluid outlet pipes 1b-1 and 1b-2 is about 100 L/min.

Perpendicularly fixed in the LED accommodating chamber 2 is a substrate 21 where multiple LED elements (light source) 22 are mounted to emit ultraviolet rays with a short wavelength of 240 to 380 nm for sterilization, disinfection, and purification and so on. In this case, the ultraviolet rays emitted from the LED elements 22 are substantially in parallel with the longitudinal axis of the casing 1.

The substrate 21 is made of heat-dissipating metal such as copper and aluminum, and the power of the LED elements 22 is supplied from the substrate 21. Note that a heat sink or heat-dissipating fins made of aluminum or the like can be provided on the back of the substrate 21. Also, a reflector with a rotating parabolic mirror can be provided to guide the ultraviolet rays from the LED elements 22 to the casing 1.

The ultraviolet rays emitted from the LED elements 22 pass through the ultraviolet transmitting window 3 to an ultraviolet irradiating chamber 12 of the casing 1. The ultraviolet transmitting window 3 is made of quartz, sapphire, fluoric resin or the like. Note that a convex lens can be provided between the LED elements 22 and the ultraviolet transmitting window 3 to converge the distribution of ultraviolet rays from the LED elements 22. Thus, the processing effect such as the sterilizing effect, the disinfecting effect, the purifying effect and so on can be enhanced.

Further, rectifying plates 41 and 42 made of metal or fluoric resin such as perfluoro-alkoxy-alkane (PFA) or perfluoro-ethilene-propene-copolymer (FEP) are provided on the upstream side in a rectifying chamber 11 of the casing 1. The rectifying plates 41 and 42, which are distant from each other by about 45 mm, are perpendicular to the longitudinal axis of the casing 1. Therefore, the casing 1 is divided into the rectifying chamber 11 and the ultraviolet ray irradiating chamber 12 separated by the rectifying plate 42. The rectifying plates 41 and 42 within the rectifying chamber 11 are operated so as to make the flow rate within the ultraviolet ray irradiating chamber 12 lower and more uniform, so that the fluid would be uniformly irradiated with ultraviolet rays from the LED elements 22 and the average ultraviolet ray irradiation amount would be higher. In this case, the fluid in the rectifying chamber 11 is also irradiated with ultraviolet rays from the LED elements 22, if the rectifying plates 41 and 42 are made of fluoric resin such as PFA or FEP for passing ultraviolet rays.

The rectifying plates 41 and 42 of FIG. 2 are explained in detail with reference to FIGS. 3A and 3B, respectively.

Figure 3A:
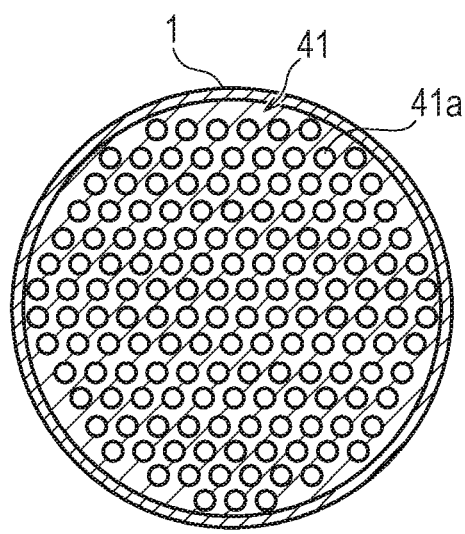
FIGS. 3A and 3B are transverse cross-sectional views taken along the lines IIIc-IIIa and IIIb-IIIb, respectively, in FIG. 2.

As illustrated in FIG. 3A, which is a front view of the rectifying plate 41, the rectifying plate 41 is circular with a center coinciding with the center axis of the casing 1, so that the rectifying plate 41 can be internally contacted at the inner face of the casing 1. The rectifying plate 41 has a large number of holes 41a whose diameter $d_1$ is about 5 mm.

Figure 3B:
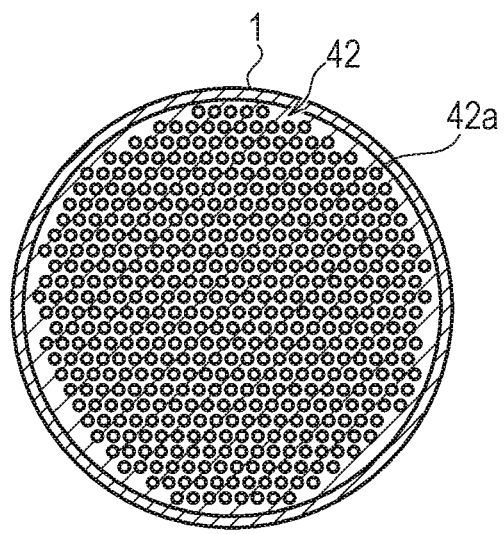

As illustrated in FIG. 3B, which is a front view of the rectifying plate 42, the rectifying plate 42 is circular with a center coinciding with the center axis of the casing 1, so that the rectifying plate 42 can be internally contacted at the inner face of the casing 1. The rectifying plate 42 has a large number of holes 42a whose diameter $d_2$ is about 2 mm.

Also, the aperture rate of the holes 42a in the rectifying plate 42 is smaller than that of the holes 41a in the rectifying plate 41, i.e., $$d_1 \cdot n_1 / S_1 > d_2 \cdot n_2 / S_2 \, (S_1 = S_2)$$

where $n_1$ is the density of the holes 41a in the rectifying plate 41;
$S_1$ is the area of the rectifying plate 41;
$n_2$ is the density of the holes 42a in the rectifying plate 42; and
$S_2$ is the area of the rectifying plate 42.

Since the aperture rate of the holes 42a is smaller than that of the holes 41a, the fluid resistance of the rectifying plate 42 is larger than that of the rectifying plate 41, so that a rectifying operation would be performed upon the fluid passed through the rectifying plate 41. Thus, the laminar effect of the fluid would be further enhanced.

Note that, if the aperture rate of the holes 42a in the rectifying plate 42 is larger than that of the holes 41a in the rectifying plate 41, the fluid in a small turbulence flow rate passed through the rectifying plate 41 would easily pass through the rectifying plate 42, so that the laminar state of the fluid passed through the rectifying plate 42 would be insufficient.

Figure 4:
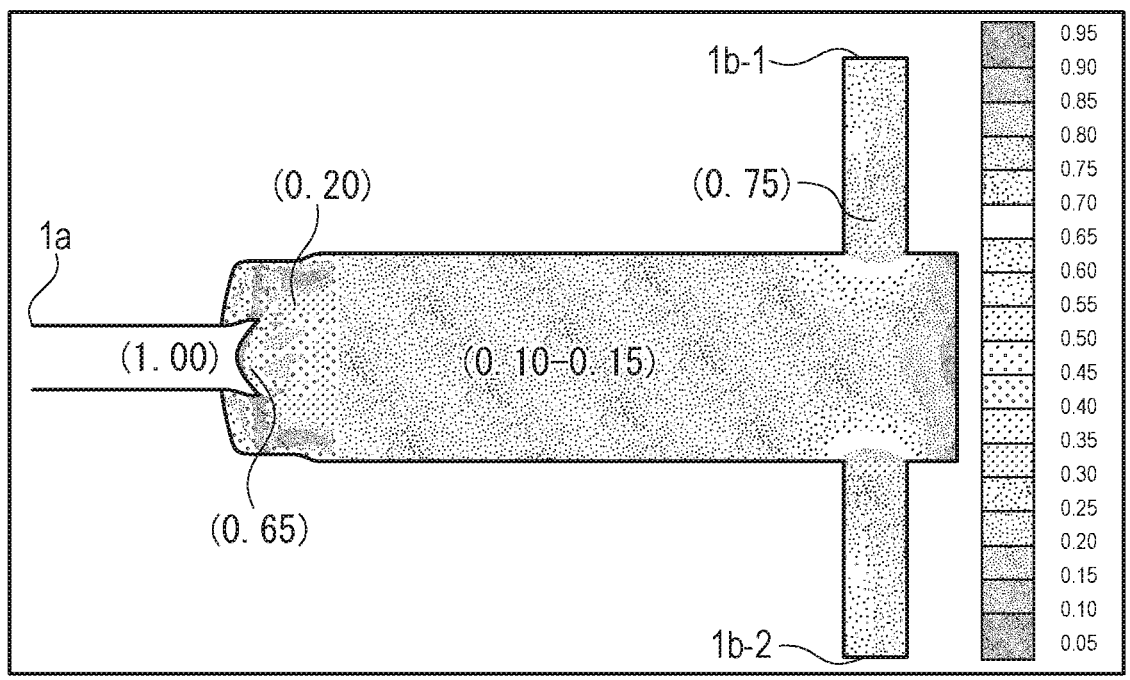
FIG. 4 is a diagram showing a simulated flow rate of fluid in the fluid processing apparatus of FIGS. 1, 2 and 3.

In FIG. 4, which shows a simulated flow rate of fluid in the fluid processing apparatus of FIGS. 1, 2 and 3, assume that the flow rate of fluid at the fluid inlet pipe 1a is 1.20 m/s. In this case, although the flow rate of fluid immediately before the rectifying plate 41 is high, i.e., 0.65 m/s (=54%), the flow rate of fluid between the rectifying plates 41 and 42 is low, i.e., 0.20 to 0.30 ms (=17 to 25%). Also, the flow rate of fluid between the rectifying plate 42 and the fluid outlet pipes 1b-1 and 1b-2 in the ultraviolet ray irradiating chamber 12 is lower, i.e., 0.10 to 0.15 m/s (=8 to 12%). Also, the flow rate of fluid at the fluid outlet pipes 1b-1 and 1b-2 is 0.75 m/s (=60%). Thus, the laminar flow rate of fluid in the ultraviolet ray irradiating chamber 12 of the casing 1 is very low and uniform.

Figure 5:
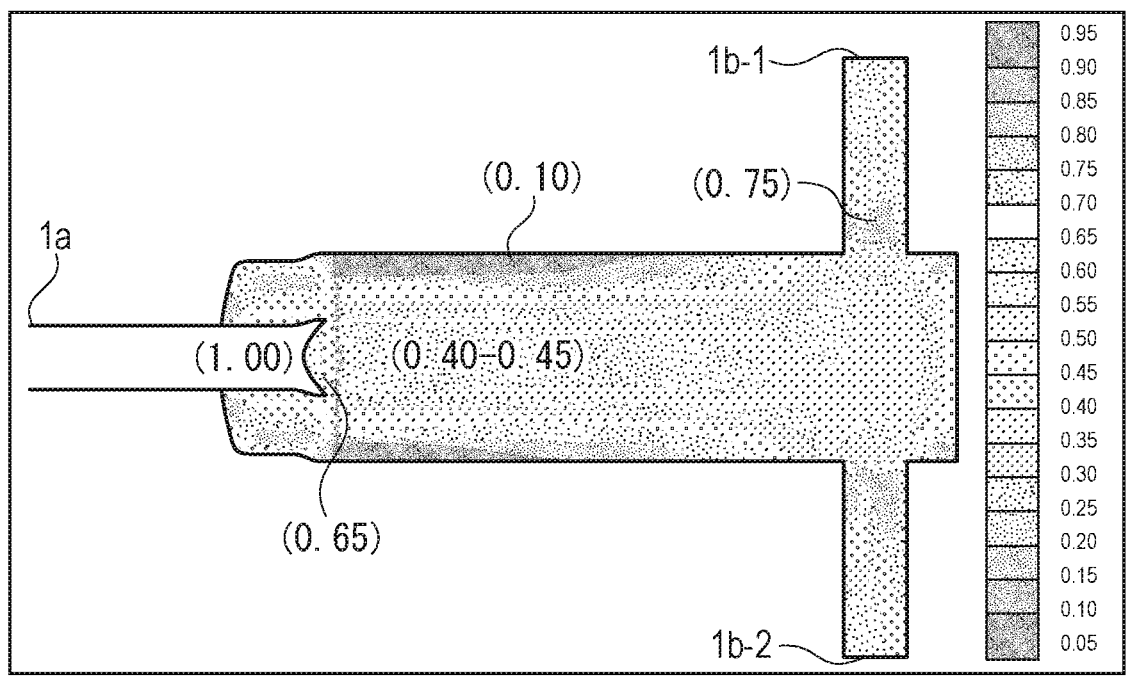
FIG. 5 is a diagram showing a simulated flow rate of fluid in a fluid processing apparatus where a single rectifying plate is provided.

Contrary to this, in FIG. 5, which shows a simulated flow rate of fluid in a fluid processing apparatus similar to the above-described second prior art fluid processing apparatus where only the rectifying plate 41 is provided while the rectifying plate 42 is not provided, assume that the flow rate of fluid at the fluid inlet pipe 1a is 1.20 m/s. In this case, the flow rate of fluid immediately before the rectifying plate 41 is also 0.65 m/s (=54%). However, the flow rate of fluid between the rectifying plate 41 and the fluid outlet pipes 1b-1 and 1b-2 is 0.10 to 0.45 m/s (=8 to 38%). In more detail, the flow rate of fluid in proximity to the inner face of the casing 1 is 0.10 (=8%), while the flow rate of fluid at the center of the casing 1 is 0.40 to 0.45 m/s (=33 to 38%). Also, the flow rate of fluid at the fluid outlet pipes 1b-1 and 1b-2 is 0.75 m/s (=60%). Thus, the laminar flow rate of fluid in the ultraviolet ray irradiating chamber 12 of the casing 1 is 0.10 to 0.45 (=8 to 38%), and therefore, it is neither low nor uniform.

Thus, the fluid processing efficiency is more excellent in the fluid processing apparatus of FIGS. 1, 2 and 3 where two rectifying plates are provided than in the fluid processing apparatus where a single rectifying plate is provided.

In FIG. 6, which illustrates a modification of the fluid processing apparatus of FIG. 2, a rectifying plate 43 is inserted between the rectifying plates 41 and 42 of FIG. 2. The rectifying plate 43, which is also made of metal or fluoric resin, is perpendicular to the longitudinal axis of the casing 1 to further make the flow rate within the ultraviolet ray irradiating chamber 12 of the casing 1 lower and more uniform.

The rectifying plates 41, 43 and 42 of FIG. 6 are illustrated in detail in FIGS. 7A, 7B and 7C, respectively.

As illustrated in FIG. 7B, which is a front view of the rectifying plate 43, the rectifying plate 43 is circular with a center coinciding with the center axis of the casing 1, so that the rectifying plate 43 can be internally touched at the inner face of the casing 1. The rectifying plate 43 has a large number of holes 43a whose diameter $d_3$ is about 3.5 mm.

As illustrated in FIGS. 7A, 7B and 7C, the diameters $d_1$, $d_3$ and $d_2$ satisfy:

$$d_1 > d_3 > d_2$$

Also, the aperture rate of the holes 43a in the rectifying plate 43 is smaller than that of the holes 41a in the rectifying plate 41 and larger than the holes 42a of the rectifying plate 42, i.e., $$d_1 \cdot n_1/S_1 > d_3 \cdot n_3/S_3 > d_2 \cdot n_2/S_2 (S_1 = S_3 = S_2)$$

where $n_3$ is the density of the holes 43a in the rectifying plate 43; and $S_3$ is the area of the rectifying plate 43.

Since the aperture rate of the holes 43a is smaller than that of the holes 41a and larger than the holes 42a, the fluid resistance of the rectifying plate 43 is larger than that of the rectifying plate 41 and smaller than that of the rectifying plate 42, so that a rectifying operation by the rectifying plate 43 would be performed upon the fluid passed through the rectifying plate 41. Thus, the laminar effect of the fluid would be further enhanced.

Figure 8A:
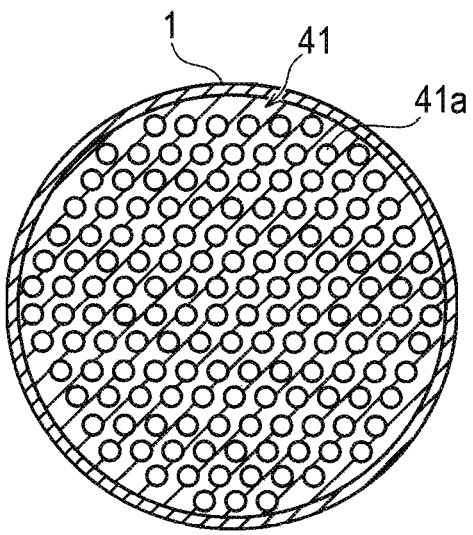
FIGS. 8A and 8B are cross-sectional views illustrating modifications of FIGS. 3A and 3B, respectively.
Figure 8B:
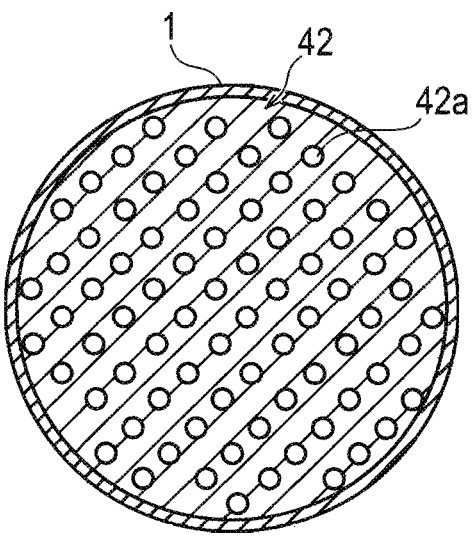
Figure 9A:
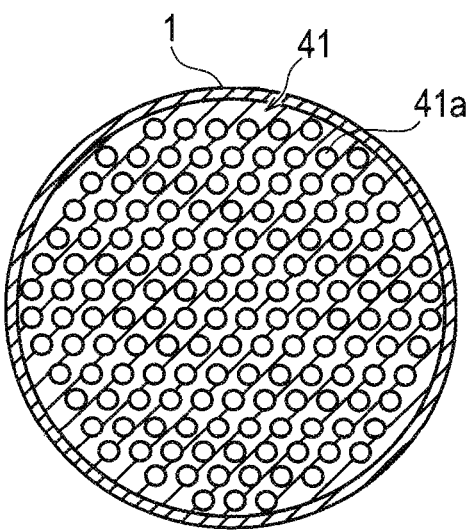
FIGS. 9A and 9B are cross-sectional views illustrating modifications of FIGS. 3A and 3B, respectively.
Figure 9B:
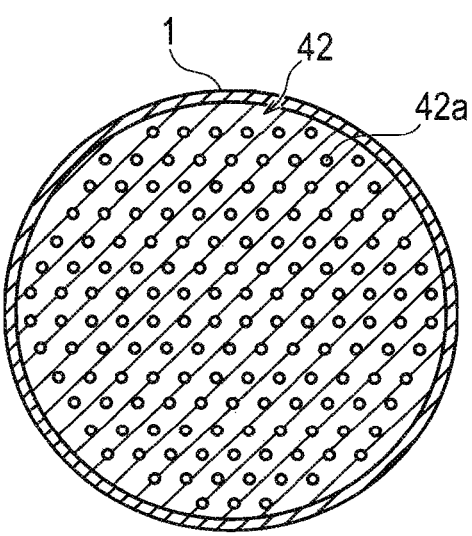

In the first embodiment, the diameters of the holes in the rectifying plates can be the same as illustrated in FIGS. 8A and 8B, which illustrate modifications of FIGS. 3A and 3B, respectively. In FIGS. 8A and 8B, the diameter $d_1$ of the holes 41a in the rectifying plate 41 is the same as the diameter $d_2$ of the holes 42a in the rectifying plate 42, i.e., $d_1=d_2=d$. In FIGS. 8A and 8B, $n_1>n_2$ is satisfied, so that the aperture rate of the holes 42a in the rectifying plate 42 is smaller than that of the holes 41a in the rectifying plate 41. Also, the densities of the holes in the rectifying plates can be the same as illustrated in FIGS. 9A and 9B, which illustrate modifications of FIGS. 3A and 3B, respectively. In FIGS. 9A and 9B, the density $n_1$ of the holes 41a in the rectifying plate 41 is the same as the density $n_2$ of the holes 42a in the rectifying plate 42, i.e., $n_1=n_2=n$. In FIGS. 9A and 9B, $d_1>d_2$ is satisfied, so that the aperture rate of the holes 42a in the rectifying plate 42 is smaller than that of the holes 41a in the rectifying plate 41. In any case, $d_1 \cdot n_1/S_1 > d_2 \cdot n_2/S_2$ is satisfied.

Generally, in the first embodiment, multiple rectifying plates with holes can be provided in the rectifying chamber 11. In this case, when a first one of the rectifying plates is closer to the fluid inlet pipe 1a than a second one of the rectifying plates, the aperture rate of the holes in the second rectifying plate is smaller than that in the first rectifying plate.

Figure 10:
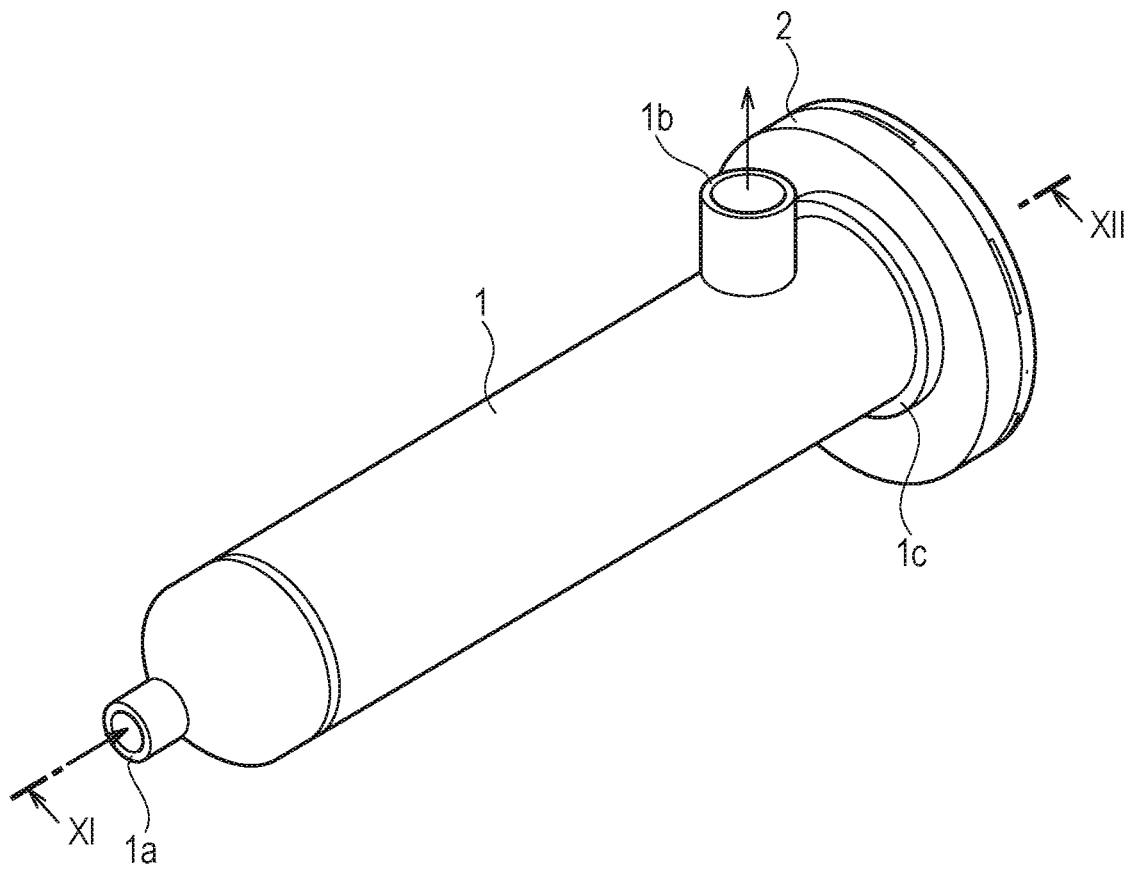
FIG. 10 is a perspective view illustrating a second embodiment of the fluid processing apparatus according to the presently disclosed subject matter.
Figure 11:
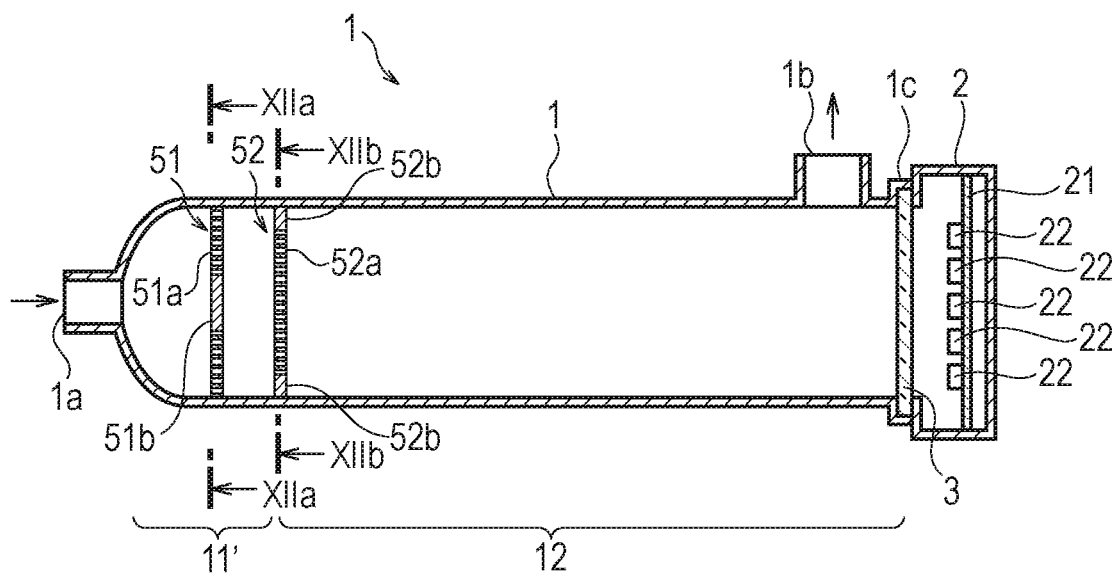
FIG. 11 is a longitudinal cross-sectional view taken along the line XI-XI in FIG. 10.

FIG. 10 is a perspective view illustrating a second embodiment of the fluid processing apparatus according to the presently disclosed subject matter, and FIG. 11 is a longitudinal cross-sectional view taken along the line XI-XI in FIG. 10.

In FIGS. 10 and 11, the casing 1 has an inner diameter of 133 mm, for example, and an outer diameter of 139 mm, for example, and is about 560 mm long, a little shorter than 580 mm. The casing 1 is provided with a fluid inlet pipe 1a on the upstream side whose diameter is 35 mm, for example, and a fluid outlet pipe 1b on the downstream side whose diameter is 35 mm, for example. The flow rate of fluid passed from fluid inlet pipe 1a through the casing 1 to the fluid outlet pipe 1b is about 100 L/min.

Further, rectifying plates 51 and 52 made of metal or fluoric resin such as PFA or FEP are provided on the upstream side in a rectifying chamber 11' of the casing 1. The rectifying plates 51 and 52, which are distant from each other by about 45 mm, are perpendicular to the longitudinal axis of the casing 1. Therefore, the casing 1 is divided into the rectifying chamber 11' and the ultraviolet ray irradiating chamber 12 separated by the rectifying plate 52. The rectifying plates 51 and 52 within the rectifying chamber 11' are operated so as to make the flow rate within the ultraviolet ray irradiating chamber 12 lower and more uniform, so that the fluid would be uniformly irradiated with ultraviolet rays from the LED elements 22 and the average ultraviolet ray irradiation amount would be lower. In this case, the fluid in the rectifying chamber 11' can be also irradiated with ultraviolet rays, if the rectifying plates 51 and 52 are made of PFA or FEP.

The rectifying plates 51 and 52 of FIG. 11 are explained in detail with reference to FIGS. 12A and 12B, respectively.

Figure 12A:
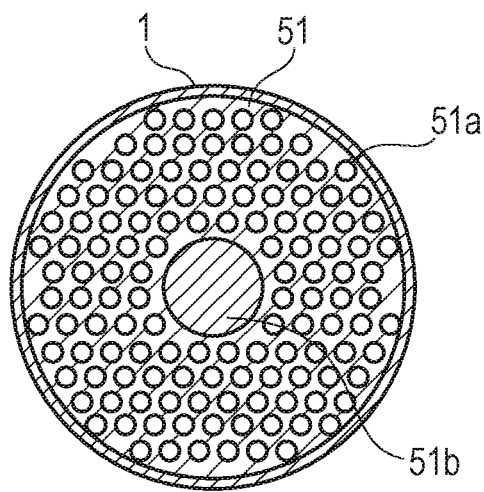
FIGS. 12A and 12B are transverse cross-sectional views taken along the lines XIIa-XIIa and XIIb-XIIb, respectively, in FIG. 11.

As illustrated in FIG. 12A, which is a front view of the rectifying plate 51, the rectifying plate 51 is circular with a center coinciding with the center axis of the casing 1, so that the rectifying plate 51 can be internally contacted at the inner face of the casing 1. The rectifying plate 51 has a large number of holes 51a whose diameter $d_1$ is about 5 mm and a fluid stream suppressing circular section 51b at the center surrounded by the holes 51a. The diameter of the fluid stream suppressing circular section 51b is not smaller than the fluid inlet pipe 1a, i.e., 35 to 40 mm.

Figure 12B:
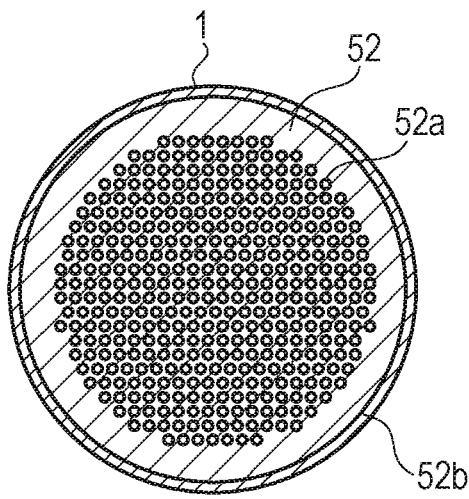

As illustrated in FIG. 12B, which is a front view of the rectifying plate 52, the rectifying plate 52 is circular with a center coinciding with the center axis of the casing 1, so that the rectifying plate 52 can be internally contacted at the inner face of the casing 1. The rectifying plate 52 has a large number of holes 52a whose diameter $d_2$ is about 2 mm and a fluid stream suppressing ring-shaped section 52b on the periphery surrounding the holes 52a.

Also, the aperture rate of the holes 52a in the rectifying plate 52 is smaller than that of the holes 51a in the rectifying plate 51, i.e., $$d_1 \cdot n_1/S_1 > d_2 \cdot n_2/S_2$$

where $n_1$ is the density of the holes 51a in the rectifying plate 51 except for the fluid stream suppressing circular section 51b; and $S_1$ is the area of the holes 51a;

$n_2$ is the density of the holes 52a in the rectifying plate 52 except for the fluid stream suppressing ring-shaped section 52b; and $S_2$ is the area of the holes 52a.

Since the aperture rate of the holes 52a in the rectifying plate 52 is smaller than that of the holes 51a in the rectifying plate 51, the fluid resistance of the rectifying plate 52 is larger than that of the rectifying plate 51, so that a rectifying operation would be performed upon the fluid passed through the rectifying plate 51. Thus, the laminar effect of the fluid would be further enhanced.

The fluid stream of the fluid processing apparatus of FIGS. 10, 11, 12A and 12B is explained next with reference to FIG. 13.

Figure 13:
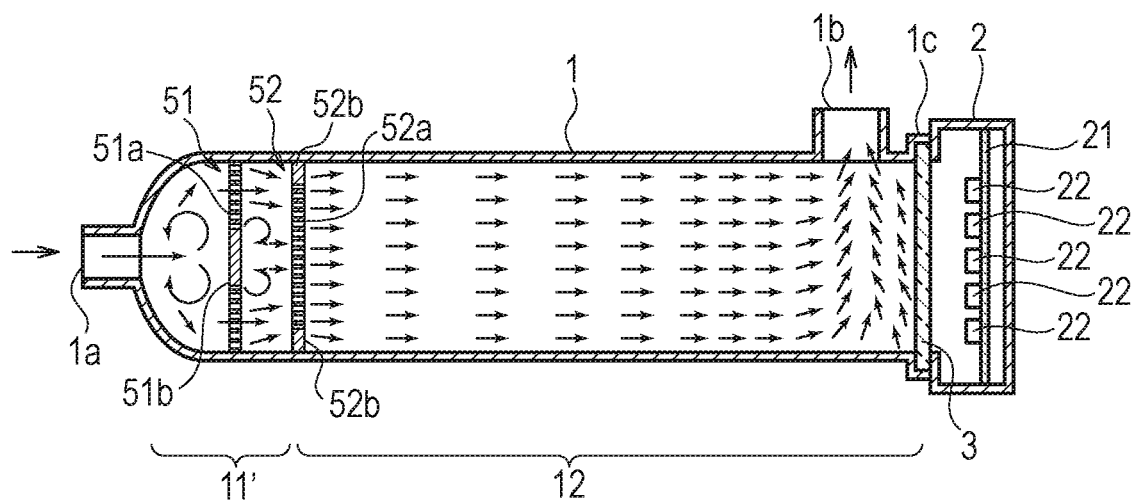
FIG. 13 is a diagram for explaining the operation of the fluid processing apparatus of FIGS. 10, 11 and 12A and 12B.

As illustrated in FIG. 13, fluid is supplied from the fluid inlet pipe 1a to collide with the fluid stream suppressing circular section 51b of the rectifying plate 51, so that the fluid would be stirred between the fluid inlet pipe 1a and the rectifying plate 51 by the fluid stream suppressing circular section 51b thereof. Then, the fluid passes through the holes 51a of the rectifying plate 51 to collide with the fluid stream suppressing ring-shaped section 52b of the rectifying plate 52, so that the fluid would be stirred between the rectifying plates 51 and 52 by the fluid stream suppressing ring-shaped section 52b of the rectifying plate 52. Finally, the fluid passes through the holes 52a of the rectifying plate 52 into the ultraviolet ray irradiating chamber 12 of the casing 1 irradiated with ultraviolet rays from the LED elements 22. In this case, the fluid stream within the ultraviolet ray irradiating chamber 12 is in a laminar flow rate state whose flow rate is lower and more uniform as compared with the first embodiment as illustrated in FIGS. 1, 2 and 3. Since the ultraviolet rays emitted from the LED elements 22 are substantially in parallel with the longitudinal axis of the casing 1, the fluid would be equally irradiated with the ultraviolet rays from the LED elements 22, which is explained with reference to FIG. 14.

Figure 14:
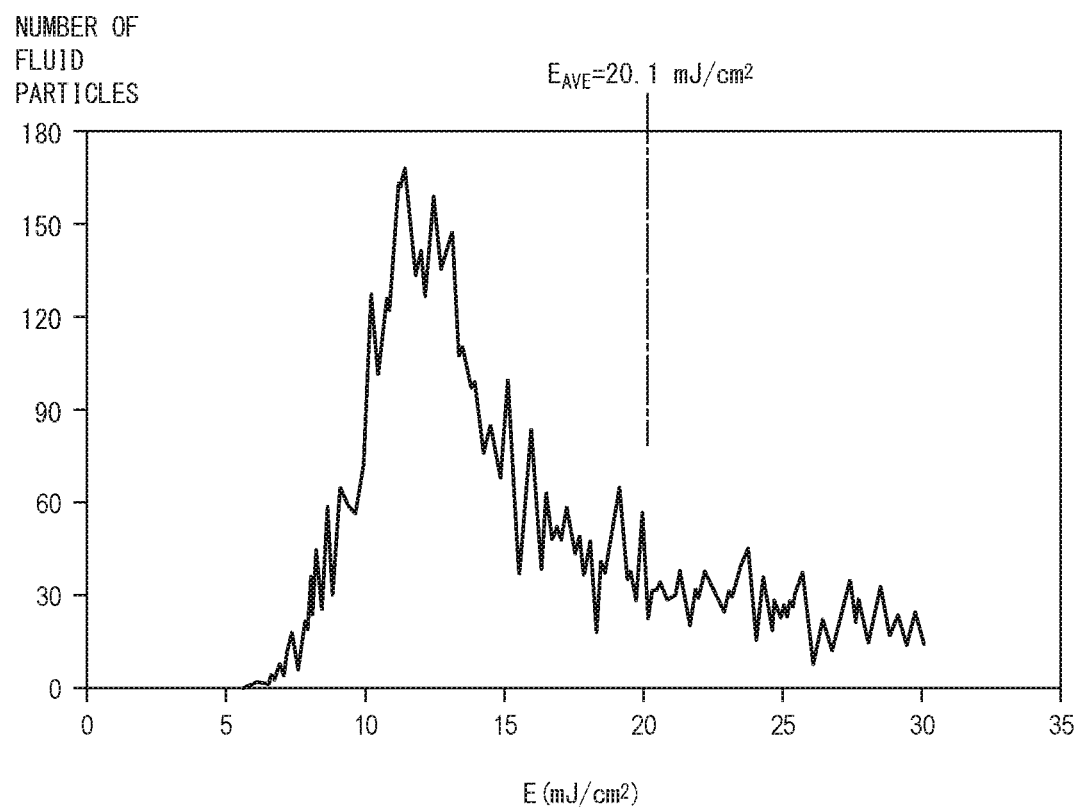
FIG. 14 is a histogram of the ultraviolet ray dose amount in the fluid processing apparatus of FIGS. 10, 11 and 12A and 12B.

In FIG. 14, assume that 3000 fluid particles at 10 L/min supplied to the casing 1 were observed by simulation while the fluid particles were irradiated with ultraviolet rays of 28J from the LED elements 22. In this case, the average dose energy $E_{AVE}$ was large, i.e., 20.1 mJ/cm$^2$.

Figure 15:
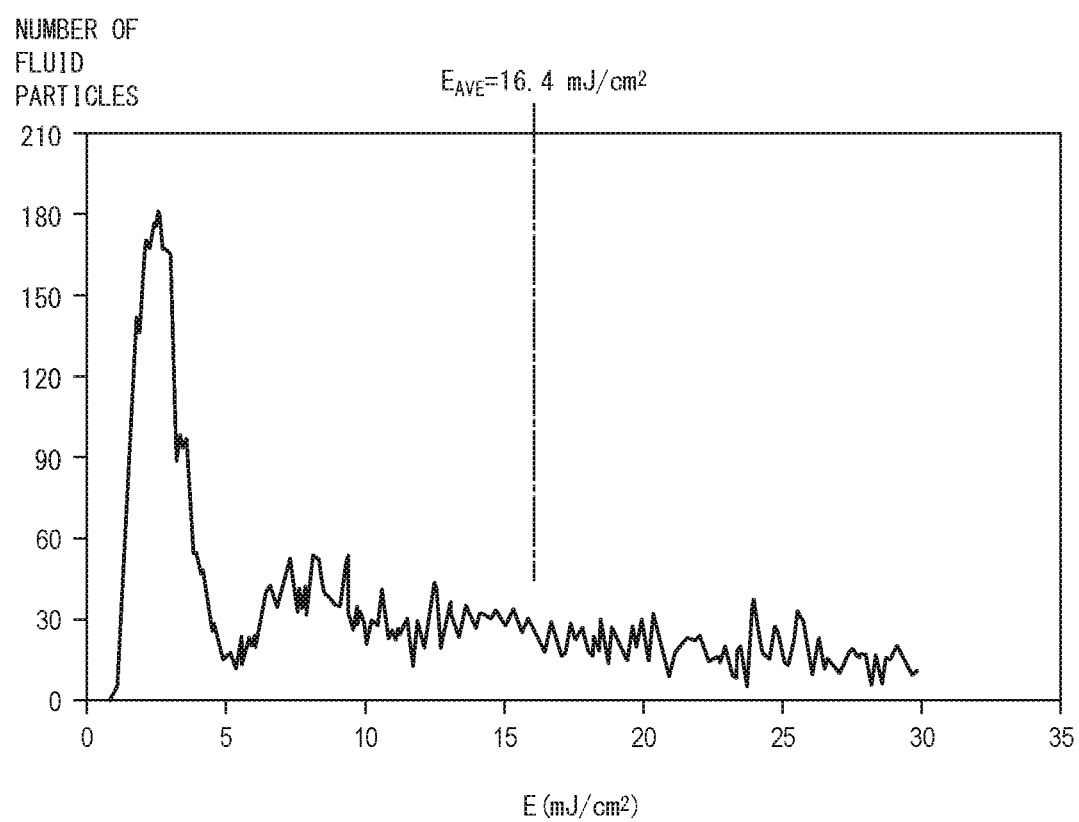
FIG. 15 is a histogram of the ultraviolet ray dose amount in a fluid processing apparatus where no rectifying plates are provided.

Contrary to this, in FIG. 15, which the dose energy characteristics of a fluid processing apparatus where no rectifying plates are provided, under the above-mentioned same condition, the average dose energy $E_{AVE}$ was small, i.e., 16.4 mJ/cm$^2$.

Figure 16A:
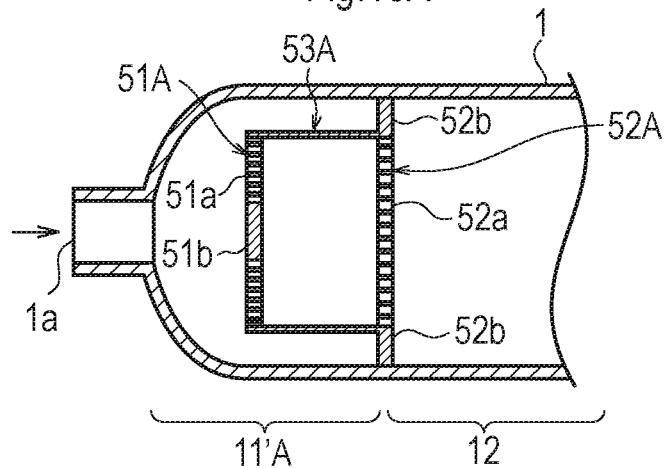
FIGS. 16A, 16B and 16C are cross-sectional views illustrating modifications of the fluid processing apparatus of FIG. 11.

In FIG. 16A, which is a first modification of the fluid processing apparatus of FIG. 11, a rectifying chamber 11'A is constructed by a rectifying plate 51A smaller than the rectifying plate 51 of FIG. 11 having the holes 51a and the fluid stream suppressing circular section 51b, a rectifying plate 52A similar to the rectifying plate 52 of FIG. 11 having the holes 52a and the fluid stream suppressing ring-shaped section 52b, and a coupling section such as a cylindrical section 53A made of metal or fluoric resin with no holes coupled between the external circumference of the rectifying plate 52A and the fluid stream suppressing ring-shaped section 52b of the rectifying plate 52A. In this case, the rectifying plate 52A is in parallel with the rectifying plate 52B by the cylindrical section 53A, and the center of the rectifying plate 52A is coincident with that of the rectifying plate 52B by the cylindrical section 53A.

When the rectifying plates 51A and 52A with the cylindrical section 53A are mounted within the casing 1, only the rectifying plate 52A is contacted internally at the inner face of the casing 1 without contacting the rectifying plate 51A at the inner face of the casing 1, thus simplifying an assembling operation of the rectifying chamber 11'A.

In the fluid processing apparatus of FIG. 16A, fluid at a high flow rate passes along the inner face of the casing 1 outside the rectifying plate 51A around the cylindrical section 53A to coincide with the fluid stream suppressing ring-shaped section 52b of the rectifying plate 52A. Thus, the high flow rate of fluid can be mitigated.

Figure 16B:
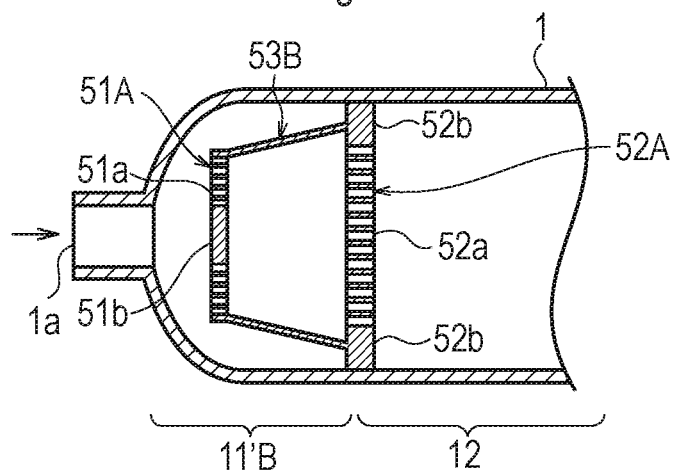

In FIG. 16B, which is a second modification of the fluid processing apparatus of FIG. 11, a rectifying chamber 11' B is constructed by a sloped (cone-shaped) cylindrical section 53B with no holes instead of the cylindrical section 53A of FIG. 16A.

In the fluid processing apparatus of FIG. 16B, more fluid at a high flow rate passes along the inner face of the casing 1 outside the rectifying plate 51A around the cone-shaped cylindrical section 53B to coincide with the fluid stream suppressing ring-shaped section 52b of the rectifying plate 52A. Thus, the high flow rate of fluid can be further mitigated.

Figure 16C:
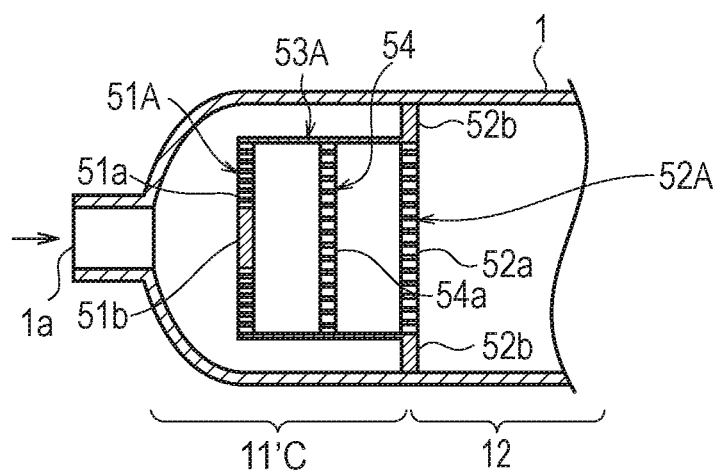

In FIG. 16C, which is a third modification of the fluid processing apparatus of FIG. 11, a rectifying chamber 11'C is further constructed by a rectifying plate 54 with holes 54a inserted between the rectifying plates 51A and 52A within the cylindrical section 53A of FIG. 16A. The rectifying plate 54, which is also made of metal or fluoric resin, is in parallel with the rectifying plates 51A and 52A to further make the flow rate of fluid within the rectifying chamber 11'C in a laminar flow state.

In FIG. 16C, the diameters $d_1$, $d_4$ and $d_2$ of the rectifying plates 51A, 54 and 52A satisfy:

$$d_1 > d_4 > d_2$$

Also, the aperture rate of the holes 54a of the rectifying plate 54 is smaller than that of the holes 51a of the rectifying plate 51A and larger than that of the holes 52a of the rectifying plate 52. Thus, the fluid resistance of the rectifying plate 54 is larger than that of the rectifying plate 51A and smaller than that of the rectifying plate 52A, thus further enhancing the laminar effect.

In FIG. 16C, a fluid stream suppressing ring-shaped section can be provided on the periphery of the rectifying plate 54 to further make the flow rate of fluid within the rectifying chamber 11'C more uniform.

In FIGS. 16A, 16B and 16C, the cylindrical section 53A can be replaced by three or more slender columns or plates.

Figure 17A:
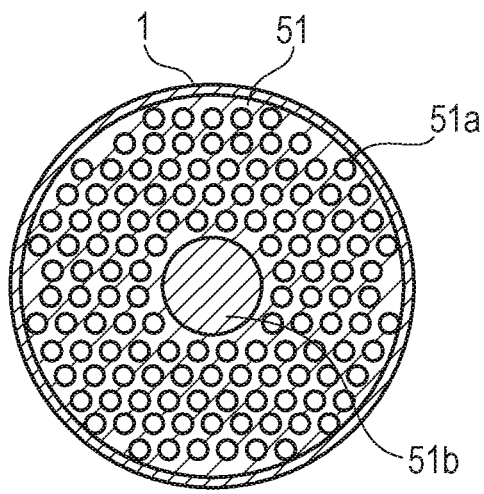
FIGS. 17A and 17B are cross-sectional views illustrating modifications of FIGS. 12A and 12B, respectively.
Figure 17B:
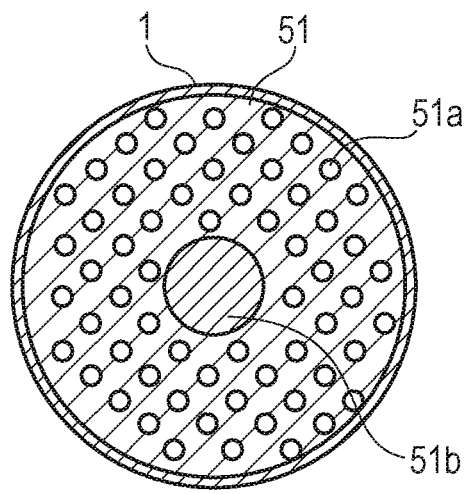
Figure 18A:
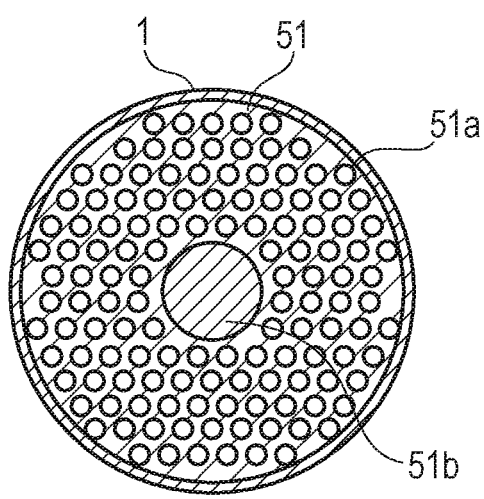
FIGS. 18A and 18B are cross-sectional views illustrating modifications of FIGS. 12A and 12B, respectively.
Figure 18B:
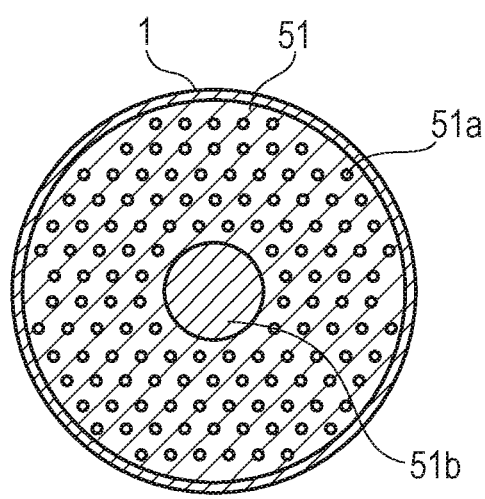

In the second embodiment, the diameters of the holes in the rectifying plates can be the same as illustrated in FIGS. 17A and 17B, which illustrate modifications of FIGS. 12A and 12B, respectively. In FIGS. 17A and 17B, the diameter $d_1$ of the holes 51a in the rectifying plate 51 is the same as the diameter $d_2$ of the holes 52a in the rectifying plate 52, i.e., $d_1 = d_2 = d$. In FIGS. 17A and 17B, $n_1 > n_2$ is satisfied, so that the aperture rate of the holes 52a in the rectifying plate 52 is smaller than that of the holes 51a in the rectifying plate 51. Also, the densities of the holes in the rectifying plates can be the same as illustrated in FIGS. 18A and 18B, which illustrate modifications of FIGS. 12A and 12B, respectively. In FIGS. 18A and 18B, the density $n_1$ of the holes 51a in the rectifying plate 51 is the same as the density $n_2$ of the holes 52a in the rectifying plate 52, i.e., $n_1 = n_2 = n$. In FIGS. 18A and 18B, $d_1 > d_2$ is satisfied, so that the aperture rate of the holes 52a in the rectifying plate 52 is smaller than that of the holes 51a in the rectifying plate 51. In any case, $d_1 \cdot n_1 / S_1 > d_2 \cdot n_2 / S_2$ is satisfied.

Generally, also in the second embodiment, multiple rectifying plates with holes can be provided in the rectifying chamber 11. In this case, when a first one of the rectifying plates is closer to the fluid inlet pipe 1a than a second one of the rectifying plates, the aperture rate of the holes in the second rectifying plate is smaller than that in the first rectifying plate.

Figure 19:
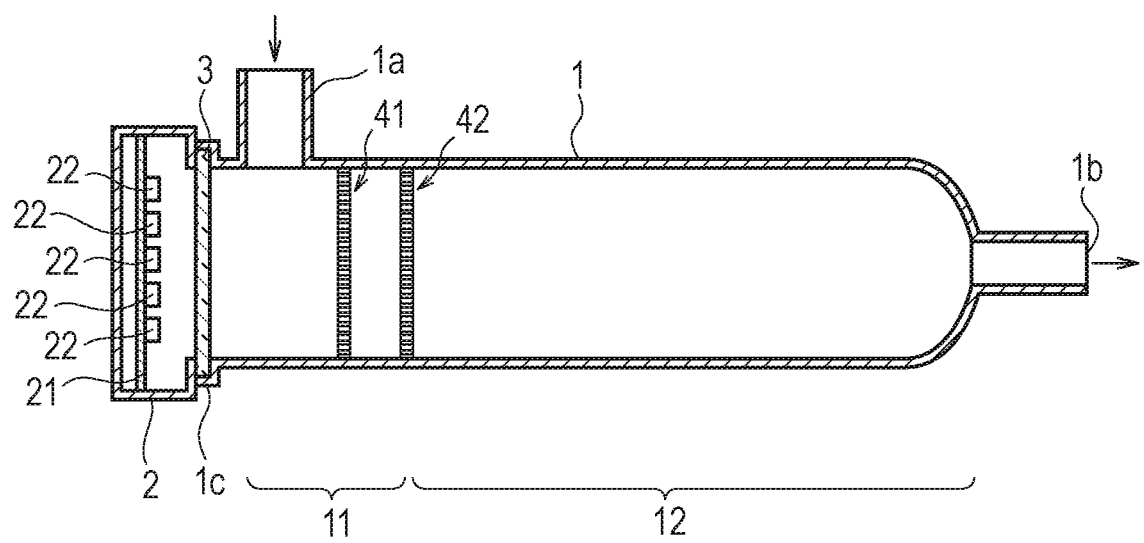
FIG. 19 is a cross-sectional view illustrating a modification of FIG. 2.

Also, in the above-described embodiments, the LED accommodating chamber 2 including the LED elements 22 (light source) is provided at the downstream side of the casing 1. However, the LED elements 22 can be provided at the upstream side of the casing 1 as illustrated in FIG. 19. In FIG. 19, the rectifying plates 41 and 42 are made of PFA or FEP for passing ultraviolet rays therethrough.

Figure 20:
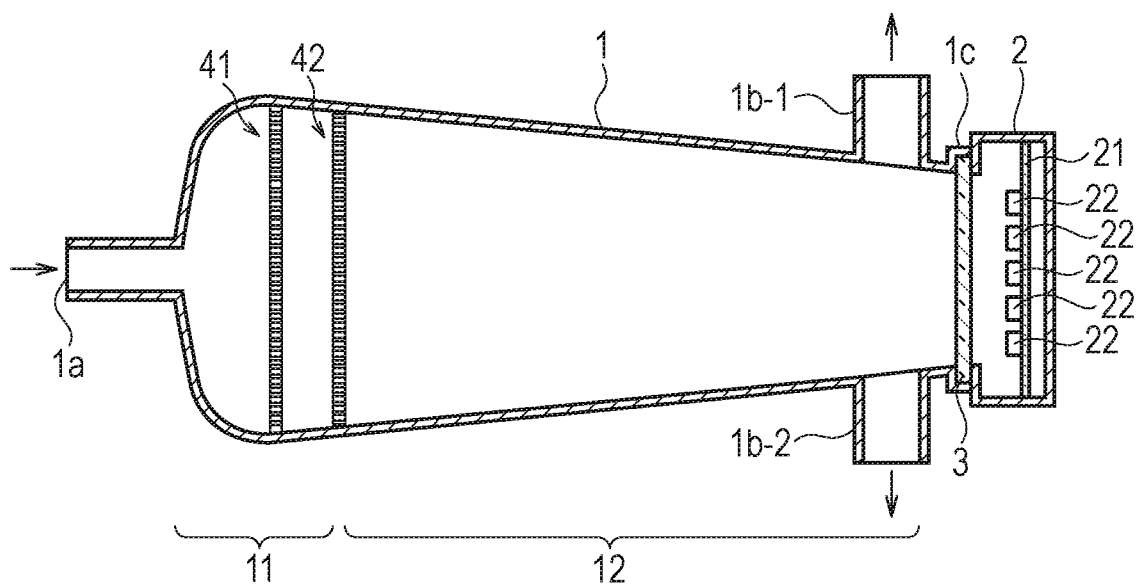
FIG. 20 is a cross-sectional view illustrating a modification of FIG. 2.

Further, in the above-described embodiments, the casing 1 is of a straight pipe type. However, the casing 1 can be of a cone shape type where the farther the distance from the LED accommodating chamber 2, the larger the diameter of the casing 1, as illustrated in FIG. 20. As a result, the fluid in the casing 1 can be sufficiently irradiated with diverged ultraviolet rays from the LED elements 22 (light source).

Figure 21A:
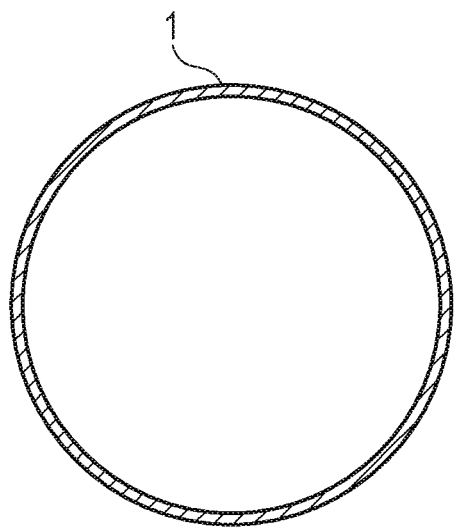
FIGS. 21A and 21B are cross-sectional views of the casing of FIG. 2.
Figure 21B:
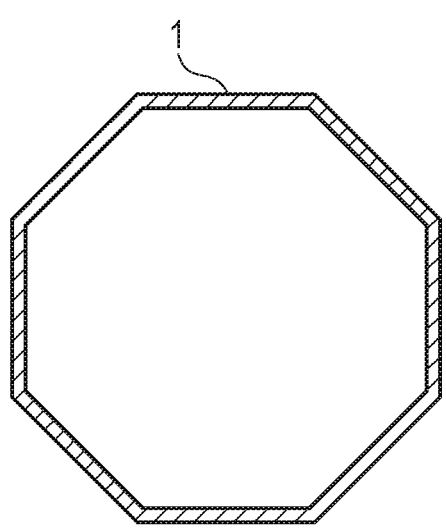

Still further, the cross section of the casing 1 can be circular or polygonal, as illustrated in FIGS. 21A and 21B.

It will be apparent to those skilled in the art that various modifications and variations can be made in the presently disclosed subject matter without departing from the spirit or scope of the presently disclosed subject matter. Thus, it is intended that the presently disclosed subject matter covers the modifications and variations of the presently disclosed subject matter provided they come within the scope of the appended claims and their equivalents. All related or prior art references described above and in the Background section of the present specification are hereby incorporated in their entirety by reference.

The invention claimed is:

1. A fluid processing apparatus comprising:
a casing having a fluid inlet pipe and a fluid outlet pipe;
multiple rectifying plates with holes in parallel with each other provided within said casing on a side of said fluid inlet pipe, said rectifying plates being perpendicular to a longitudinal axis of said casing; and
a light source for irradiating fluid passing from said fluid inlet pipe through said casing to said fluid outlet pipe with ultraviolet rays,
wherein, when a first one of said multiple rectifying, plates is closer to said fluid inlet pipe than a second one of said multiple rectifying plates, a diameter of the holes in said second rectifying plate is smaller than a diameter of the holes h said first rectifying plate.

2. The fluid processing apparatus as set forth in claim 1, wherein said first and second rectifying plates are contacted internally at an inner face of said casing.

3. The fluid processing apparatus as set forth in claim 1, wherein said first rectifying plate comprises a fluid stream suppressing section, centered at said casing, whose diameter is not smaller than a diameter of said fluid inlet pipe.

4. The fluid processing apparatus as set forth in claim 1, wherein said second rectifying plate comprises a fluid stream suppressing section at a periphery surrounding the holes of said second rectifying plate.

5. The fluid processing apparatus as set forth in claim 4, further comprising a coupling section that couples said first rectifying plate to said second rectifying plate,
said second rectifying plate being contacted internally to an inner face of said casing.

6. The fluid processing apparatus as set forth in claim 5, wherein said coupling section comprises a cylindrical section with no holes.

7. The fluid processing apparatus as set forth in claim 5, wherein said coupling section comprises a cone-shaped cylindrical section with no holes.

8. The fluid processing apparatus as set forth in claim 1, wherein said light source is provided at either a downstream side or an upstream side of said casing.

9. The fluid processing apparatus as set forth in claim 1, wherein the farther the distance from said light source, the larger the cross section of said casing.

10. The fluid processing apparatus as set forth in claim 1, wherein said cylindrical casing has a larger inner diameter than a diameter of said fluid inlet pipe, and a center of said cylindrical casing coincides with a center of said fluid inlet pipe.

11. The fluid processing apparatus as set forth in claim 1, wherein said light source comprises multiple light emitting diode elements each for emit ultraviolet rays with a wavelength of 240 to 380 nm.

12. The fluid processing apparatus as set forth in claim 1, wherein said ultraviolet transmitting window is adapted to receive said ultraviolet rays via a reflector or via a convex lens from said light source.

13. The fluid processing apparatus as set forth in claim 1, wherein said rectifying plates comprise metal of fluoric resin.

14. The fluid processing apparatus as set forth in claim 1, further comprising another light source provided on an upstream side of said rectifying chamber to irradiate fluid passing from said fluid inlet pipe to said rectifying chamber with ultraviolet rays, said rectifying plates comprising perfluoro-alkoxy-alkane or perfluoro-ethilene-propene for passing ultraviolet rays therethrough.

15. A fluid processing apparatus comprising:
a cylindrical casing having a fluid inlet pipe and a fluid outlet pipe;
multiple rectifying plates with holes in parallel with each other provided within said casing on a side of said fluid inlet pipe, said rectifying plates being perpendicular to a longitudinal axis of said casing; and
a light source for irradiating fluid passing from said fluid inlet pipe through said casing to said fluid outlet pipe with ultraviolet rays,
said multiple rectifying plates comprising at least a first rectifying plate on a side of said fluid inlet pipe and a second rectifying plate distant from said first rectifying plate on a downstream side of said first rectifying plate, a diameter of the holes of said first rectifying plate being larger than a diameter of the holes of said second rectifying plate,
said cylindrical casing being divided by said second rectifying plate into a rectifying chamber and an ultraviolet ray irradiating chamber,
said fluid inlet pipe and said first rectifying plate being provided h said rectifying chamber,
an ultraviolet transmitting window being provided in said ultraviolet ray irradiating chamber opposing said second rectifying plate for passing said ultraviolet rays from said light source into said ultraviolet ray irradiating chamber, thus irradiating fluid in said ultraviolet ray irradiating chamber with said ultraviolet rays,
said fluid outlet pipe being provided between said second rectifying plate and said ultraviolet transmitting window.

16. The fluid processing apparatus as set forth in claim 15, wherein, an aperture rate of the holes in a third one of said multiple rectifying plates is between an aperture rate of the holes in said first rectifying plate and an aperture rate of the holes in said second rectifying plate.

17. The fluid processing apparatus as set forth in claim 15, wherein said first and second rectifying plates are contacted internally at an inner face of said casing.

18. The fluid processing apparatus as set forth in claim 15, wherein said cylindrical casing has a larger inner diameter than a diameter of said fluid inlet pipe, and a center of said cylindrical casing coincides with a center of said fluid inlet pipe.

19. The fluid processing apparatus as set forth in claim 15, wherein said light source comprises multiple light emitting diode elements each for emit ultraviolet rays with a wavelength of 240 to 380 nm.

* * * * *